(12) United States Patent
Caldironi

(10) Patent No.: US 6,645,231 B1
(45) Date of Patent: Nov. 11, 2003

(54) APPARATUS FOR THE CONTROLLED GENERATION OF ULTRAVIOLET RAYS FOR FOCUSED MICRO STIMULATION OF CELLS

(75) Inventor: Franco Caldironi, Cunardo (IT)

(73) Assignee: Biophoenix SRL, Milan (IT)

( * ) Notice: Subject to any disclaimer, the term of this patent is extended or adjusted under 35 U.S.C. 154(b) by 0 days.

(21) Appl. No.: 09/564,651

(22) Filed: May 3, 2000

(30) Foreign Application Priority Data

May 12, 1999 (IT) .......................................... MI99A1035

(51) Int. Cl.[7] ................................................. A61N 5/06
(52) U.S. Cl. .................................. 607/94; 607/88; 606/2
(58) Field of Search ........................... 606/2, 3, 4, 5, 606/9; 607/88, 89, 94

(56) References Cited

U.S. PATENT DOCUMENTS 4,732,148 A * 3/1988 L'Esperance, Jr. .............. 606/5
4,930,504 A * 6/1990 Diamantopoulos et al. ... 607/88
5,376,086 A * 12/1994 Khoobehi et al. .............. 606/4
5,968,036 A * 10/1999 Goodman et al. ............ 606/12

* cited by examiner

Primary Examiner—Roy D. Gibson
(74) Attorney, Agent, or Firm—Young & Thompson

(57) ABSTRACT

An apparatus for the controlled generation of ultraviolet rays for a focused micro stimulation of cell structures. The apparatus comprises an ultraviolet ray beam generator, at a frequencies comprised between 200 and 400 nm; means for focusing a ray beam on a selected surface area of the cell structure, and a protective masking member in a non reflective material adhered to the cell structure; the masking member comprises at least one perforated zone to expose the selected surface area of the cell structure, to be stimulated by the focused ray beam, and a programmable control unit for metering the ultraviolet energy of the generator radiated on the selected area during a period of time.

20 Claims, 3 Drawing Sheets

APPARATUS FOR THE CONTROLLED GENERATION OF ULTRAVIOLET RAYS FOR FOCUSED MICRO STIMULATION OF CELLS

BACKGROUND OF THE INVENTION

The present invention relates to an apparatus for the controlled generation of ultraviolet energy (UV) and for micro stimulation by electromagnetic rays on selected area of biological cells; the invention is particularly suitable for the focused micro stimulation of any biological cell structure, for example for biological cell stabilization and reactivation, or for other treatments for which the use of an ultraviolet ray apparatus according to the invention is of particularly efficiency in alternative for conventional systems.

For the purposes of this description, the expression "focused micro stimulation of biological cell surface" refers to the controlled generation of an ultraviolet ray beam included in a specific range of ultraviolet frequencies, which are focused on an appropriately selected biological cell surface area, which has to be stimulated with a metered quantity of electromagnetic energy.

The invention resides in an apparatus comprising in combination an UV generator and energy control means for stimulation of selected surface areas of a biological cell structure; one of its possible applications will be described in greater detail hereinbelow with reference to the re-pigmentation of biological cell structures, for restoring the physical appearance without this having to be understood as limiting in respect of other possible applications and uses of the invention.

STATE OF THE ART

As is known, natural or artificial ultraviolet rays have wavelengths between 200 and 400 nm approximately and, the higher the frequency, the greater their capacity to penetrate a cell structure.

Various attempts have been made in the past to use ultraviolet rays in a generalized form for the reactivating or for the stimulation of biological cell structures. However the repeated shower application of ultraviolet rays, in an uncontrolled manner entails the absorption of excess rays over large surfaces and in zones not involved by the treatment, as well as an excessively long exposure times with increased risks of negative reactions.

The conventional ultraviolet ray systems have not therefore enabled appreciable and long-lasting results to be obtained, due to the impossibility of having suitable apparatus and means designed to allow their selective and controlled use, i.e. such as to achieve a selective action on surface areas of biological cell structures capable of receiving and using light energy for triggering those mechanisms whereby it is possible to facilitate or restore the biological activity or activation of the cells.

OBJECTS OF THE INVENTION

Therefore the general object of the present invention is to provide an apparatus for the controlled generation of ultraviolet rays, suitable for focused micro stimulation of specific biological cell surfaces, by means of metered electromagnetic energy in one or more specific ultraviolet frequency bands, such as to allow a particular efficacy and long-lasting effects. A further object of the present invention is to provide apparatus for the controlled generation of ultraviolet rays which, in addition to allowing a focused irradiation of the cell surface zones to be treated, also allows the position and features of the same surface zones, to be envisaged and selected in advance and in a distinctly definite manner.

Yet another object of the present invention is to provide apparatus for controlled generation of ultraviolet rays for cell stimulation as stated above, which can be appropriately programmed and set to adjust its working parameters, in addition to correctly checking its operation mode, in the focused treatment by ultraviolet rays with a variable UVA and UVB percentage.

An additional object is to provide an apparatus for the focused micro stimulation with a metered emission of ultraviolet rays which, in addition to the programming and control of the radiating energy emitted by the apparatus, allows also a selective control of the radiated energy on a selected area of a biological cell surface to be treated.

BRIEF DESCRIPTION OF THE INVENTION

The above, in focused micro stimulation with ultraviolet rays of biological cell structures, can be achieved by means of an apparatus according to the invention comprising in combination an (UV) ultraviolet generator for generation of ultraviolet rays in a specific UV frequencies band, and a masking element of particular features and designs.

BRIEF DESCRIPTION OF THE DRAWINGS

The apparatus for the controlled generation of ultraviolet rays which can be used in the micro stimulation of biological cell structures, and various forms of masking element, will be illustrated in greater detail hereinbelow with reference to the accompanying drawings, in which.

DETAILED DESCRIPTION OF THE INVENTION

Figure 1:
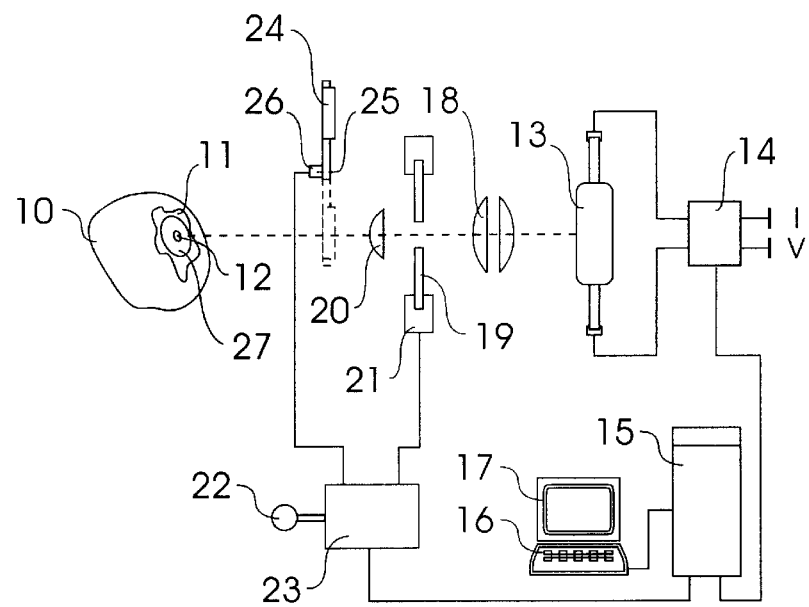
FIG. 1 is a general diagram of the apparatus.

Reference number 10 in FIG. 1 denotes a generic body having a biological cell zone 11 which has to be subjected to micro stimulation by ultraviolet rays (UV), for example in order to restore the original colouring of the pigmentation.

As schematically shown, the apparatus comprises an ultraviolet ray source 13, provided by a special lamp capable of generating in a controlled manner a beam of ultraviolet rays having an high percentage content of electromagnetic radiation, in the band of frequencies between 200 and 400 nm, preferably between 260 and 300 nm.

The lamp 13 is connected to an adjustable power supply 14 which can be regulated in terms of current I or voltage V by a programmable control unit 15 to change the radiation power and various working parameters of the apparatus in relation to specific requirements of use. This can be achieved by operating for example via a control console 16, provided with an appropriate display 17.

In line with the lamp 13, the apparatus comprises a first optical system 18 for concentration of the UV rays, an adjustable diaphragm or shutter 19, and a second optical system 20 for focusing of the beam of rays generated by the lamp 13 on a reference plane or surface corresponding to a restricted zone 12 of the biological cell zone 11 to be treated. The apparatus could also be provided with a flexible liquid light-guide, not shown, for example by a fibre or a bundle of fibres known as water fibres, for better focusing the ray beam on the restricted surface 12 to be stimulated, without having to move the apparatus.

Opening and closure of the shutter 19 causes a widening or narrowing of the ray beam towards the surface 11 to be irradiated, to adjust its radiated energy. Opening and closure of the shutter 19 can be achieved by means of an appropriate motor drive 21, for example an air motor drive which can be connected to a pressurised air source 22 via an interface 23 operatively connected to the control unit 15.

Reference 24 in FIG. 1 also denotes a special black light or WOOD filter, which can be positioned in front of the optical system 20 for the generation of a fluorescent light designed to locate and evaluate the condition of the surface area 11 of the biological cell structure to be treated.

The WOOD filter 24 can be positioned in front of the optical system 20, making it rotate for example around an axis 25 controlled by an air motor 26, or another drive means.

Finally reference 27 in FIG. 1 denotes a special light mask in an opaque or non-reflecting material, intended to surround and define the limited zone 12 of the biological cell surface 11 to be treated, masking and protecting the same except for the selected zone 12. Features and some masking elements 27 will be described further here in below with reference to FIGS. 4 to 9.

A feature of the apparatus according to the invention, in addition to means for generation of UV rays and means for defining the zone to be radiated, consists of the possibility of varying and controlling the band of ultraviolet frequencies of the ray beam generated by the apparatus, and the percentage content of electromagnetic rays generated.

This will be made clearer hereinunder with reference to the graphs of spectral distribution of the ultraviolet rays of FIGS. 2 and 3.

During extensive and thorough experiments, it was in fact discovered that good and long-lasting results are obtained if focused micro stimulation of the biological cell zone 11 to be treated, is performed by means of a controlled beam of rays which has to be focused on a small or point-shaped area, or on a defined and restricted zone of biological cell stimulation, and if the percentage content of rays of the generated beam comes within the UVA and UVB ultraviolet frequencies bands, preferably between 260 and 320 nm, and by providing an appropriate masking around the cell zone to be treated, avoiding the ray beam to be reflected by the masking, as specified further below.

Figure 2:
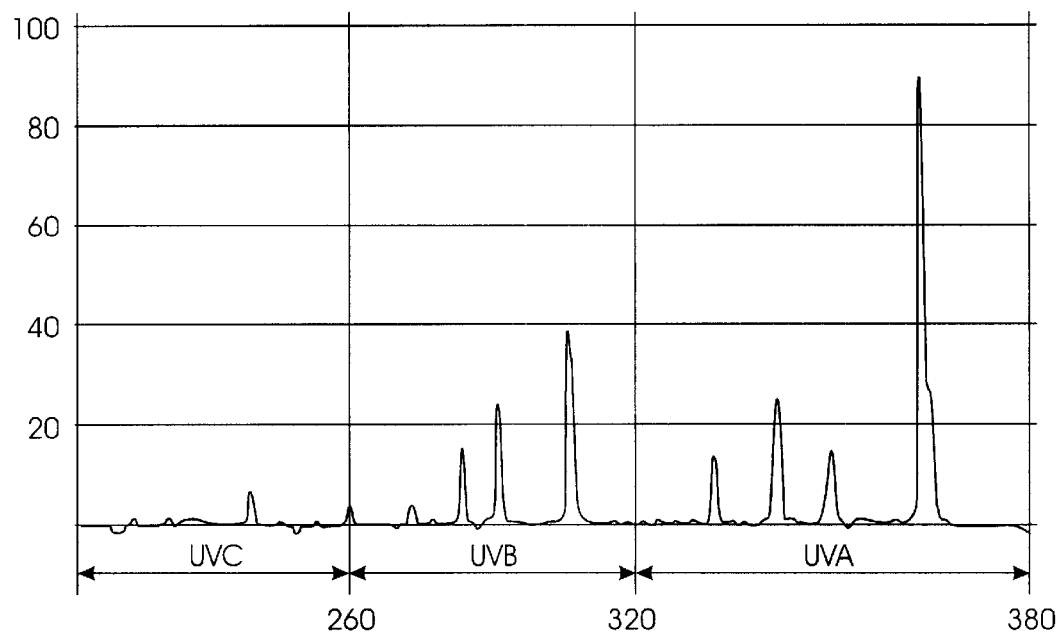
FIG. 2 is a graph illustrating the spectral distribution of the ultraviolet rays in conventional UV generators.

More specifically, a conventional UV lamp has a spectral distribution of the ultraviolet rays of the type shown in FIG. 2. From this Figure it can been seen that most of the radiation, equal to 70–80%, are included in the UVA band between 315 and 380 nm, while the remaining percentage part is substantially included in the central band of UVB radiation between 280 and 315 nm, the band of UVC rays being totally negligible.

Figure 3:
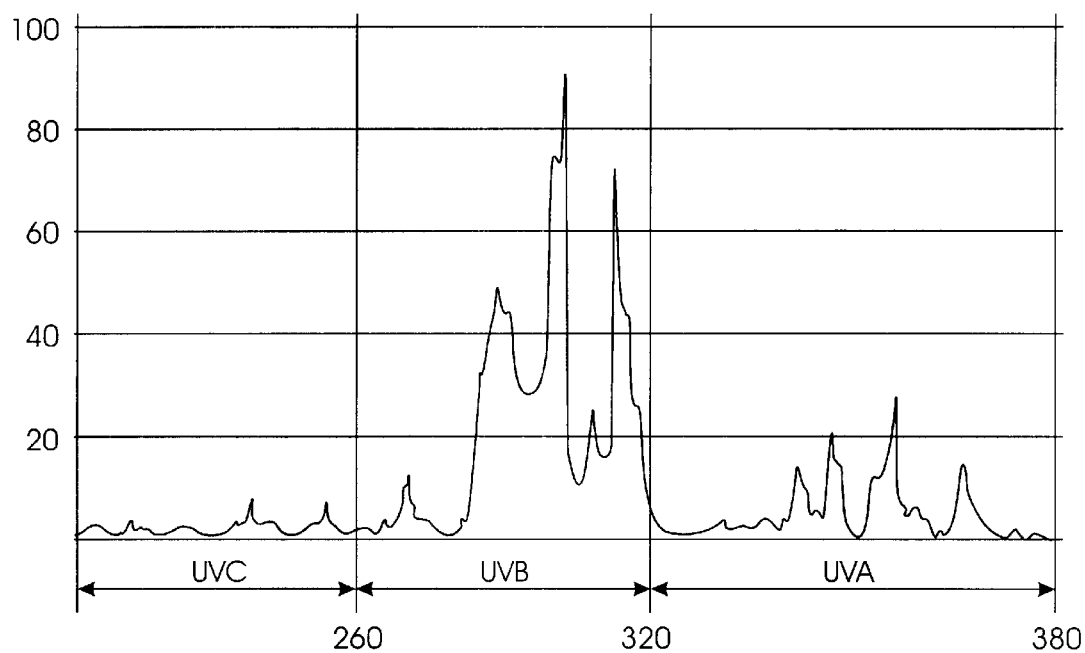
FIG. 3 is a graph illustrating the spectral distribution of ultraviolet rays in an UV generator for an apparatus according to the invention.

Differently from FIG. 2, FIG. 3 shows. a higher percentage content of ultraviolet rays, equal to approximately 60–85%, included in the central band of UVB rays, between 280 and 320 nm approximately, while there is a lower content, in percentage terms of UVA and UVC.

It has been also discovered that in micro stimulation by ultraviolet rays of biological cell structures with an apparatus according to the invention, it is likewise important to control certain working parameters of the apparatus, in particular the voltage V supplied to the lamp 13 for generation of the ray beam, and the value of the current I flowing in the lamp, in addition to the supply time. In general it is necessary to adjust and control the quantity of energy supplied to the cell structure and the mode of supplying the energy itself which may be of a linear or continuous type, or of the pulsed type. All this is achieved not only by controlling the voltage values and current flowing in the lamp 13, but also by controlling the opening time of the shutter 19, that is the quantity of energy radiated on the cell surface to be treated; this may be performed by means of the control unit 15, which in this respect is made appropriately programmable by an operator working on the keyboard 16 of the control console, whose set data can be seen in operative tables which appear on the display 17.

The control unit 15 can also be programmed to show other operating parameters or data, for example the value of the radiated energy, the temperature of the lamp 13, and/or special video display tables. In particular the control unit may be programmed to store the tables containing characteristic details of the subject undergoing treatment; the video topographical skin data relating to the body zones, the form and/or distribution of the various surface areas to be treated in the same subject; the percentage and total quantification thereof; the video skin iconographic charts relating to a digitalised, progressive and chronologically organised recording of the surfaces being treated; the video skin colour charts relating to a numerical recording of the variations in colour or another physical feature of the biological cell structure treated; and the working charts of the same apparatus.

The operation and use of the apparatus described above are briefly the following:

After having switched on the generator 13, 14 for the ultraviolet rays, if necessary the WOOD filter 24 is positioned in front of the lens 20 for concentration of the UVB rays in order to cause emission of a fluorescent light at a specific frequency of the diagram of FIG. 3.

With the apparatus in these conditions it is possible to explore the entire surface 11 of the biological cell surface 10 to be treated, and identify a restricted zone 12 which is to be micro-stimulated in a controlled manner by means of a UVB ray beam generated by the apparatus of FIG. 1. Having identified the micro stimulation zone 12, a non-reflecting material 27, also cited as masking element, is applied on the surface 11 in order to leave only the restricted surface zone 12 uncovered, masking and protecting the surrounding zones. At the same time all the necessary working parameters, such as the power of emission of the ultraviolet ray source, the amplitude of the light beam to be generated, the distance of the lens 20 from the zone 12 to be micro-stimulated and the exposure time are set and adjusted via the control console 16.

Having set up the apparatus in this way, an UVB ray beam can then be emitted and a focused treatment performed for the time and with the energy emission values previously set, all this with automatic control and programming by the control unit 15.

The ray beam may be emitted in continuous or pulsed mode; moreover the treatment may be repeated once or several times, at preset intervals of time, modifying or adjusting on each time the working parameters of the apparatus and the emission mode of the same ray beam. At the same time all the data set on the apparatus and the state of the treated zone or zones may be stored in special working charts or tables, or in videographic charts which can, when required, be called up and displayed on the display 17.

As previously referred, the apparatus according to the invention comprises the combination of a ray generator for controlled generation of ultraviolet rays for the micro stimulation of a biological cell structure, and a special masking element 27 suitable for defining one or more restricted surface areas to be treated and for protecting the surrounding zones, such as to optimise the effect of the ultraviolet rays.

The structural and form features of the masking element 27 are now described with reference to the detail of FIG. 4 and to some specific embodiments represented in the remaining FIGS. 5 to 9.

As referred previously, the masking element 27 must not have light reflecting properties, that is to say it must consist of a material, or have a light absorbing surface facing towards the source of UVB rays, such as a dark coloured, or preferably black surface, in a material having a low reflection index at the frequencies concerned.

Figure 4:
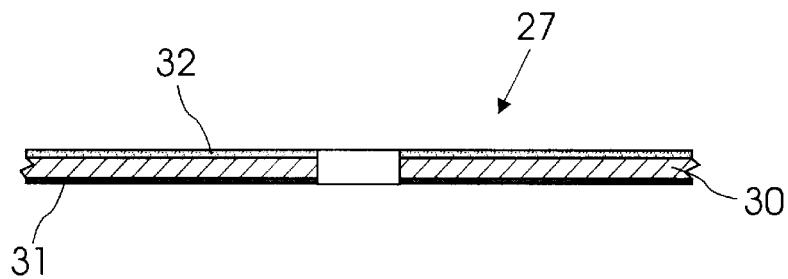
FIG. 4 is an enlarged cross-sectional view of a masking member.

As shown in FIG. 4, the masking element is for example in the form of a thin film 30, in plastic material, having a thickness, for example, between 0.4 and 0.7 mm, provided with a rear self-adhesive layer 31 normally protected by a removable film.

The film 30 of plastic material provide a substrate for a front layer 32 of any opacifying and non-reflecting material, in a dark colour, preferably black, comprising for example a velvet-like layer made to adhere to the film 30.

The film 30 and the velvet-like layer 32 of the masking element have in turn one or more holes or perforations of varying shape or sizes, varyingly arranged on the masking element which define the shape of the surface or surfaces to be treated. In this respect, when use is made of holes or perforations of a small diameter or cross dimensions, intended to define a small surface area, it is important that the thickness of the film 30 and of the opacifying layer 32 be maintained as small as possible, within the values indicated previously, to avoid backwards reflection.

Any shapes and dimensions of the mask element 27, and any shapes, dimensions and number of the holes or apertures, defining the surface zone 12 to be radiated, as well as their arrangement, can be adopted and varied according to specific needs.

Some possible forms of mask elements are shown by way of an example in FIGS. 5 to 9 of the accompanying drawings.

Figure 5:
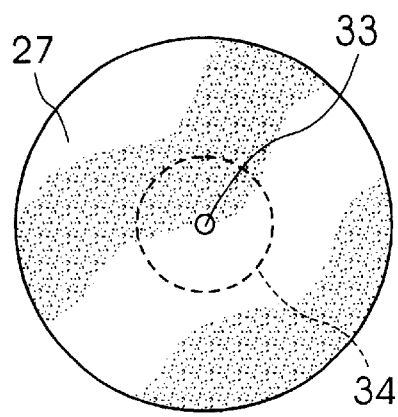
FIGS. 5 to 9 show a top view of some of the numerous embodiments of masking elements according to the invention.

FIG. 5 shows a mask element 27 of circular shape, having a diameter between, for example, 60 and 80 mm, provided with a single central hole 33, small in diameter. The dimensions of the central hole 33 may vary from a diameter equal to or smaller than one millimetre, to considerably higher diameters, as outlined by 34 in FIG. 5, for example up to 250 mm or above. Since the quantity of energy radiated on the cell surface to be treated depends both on the dimensions and on the number of holes, it is more convenient to talk in terms of total radiation surface for the mask element.

Therefore, in the case of a mask element with a single hole in FIG. 5, the radiated surface area can indicatively vary from 3 mm$^2$ up to 500 mm$^2$ and above.

As referred previously, the mask element 27 may have a different number of holes, of the same and/or different dimensions, otherwise arranged and aligned to adapt to the shape and/or dimensions of the surface to be treated, according to the quantity of radiating energy to be supplied.

Figure 6:
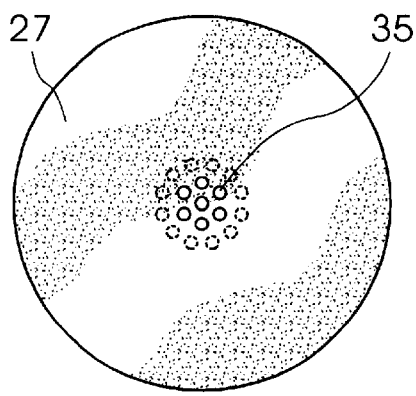
Figure 7:
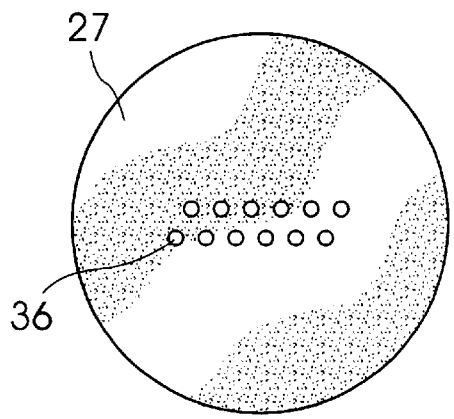
Figure 8:
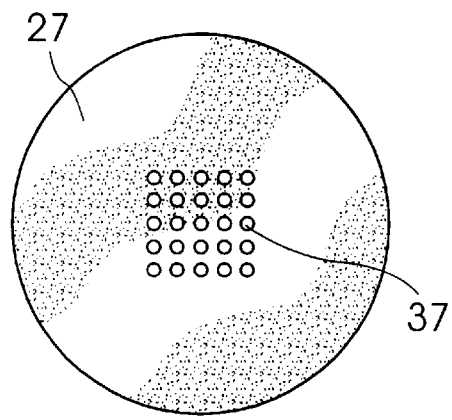

FIGS. 6, 7 and 8 show some examples of circular mask elements 27 in which the mask element of FIG. 6 comprises a plurality of holes 35 arranged along one or more concentric circumferences, with holes of the same or of different diameters.

FIG. 7 shows instead a mask element 27, again with a circular shape, with holes 36 aligned on two parallel rows, while FIG. 8 shows again a circular mask element 27 with holes 37 aligned and arranged in a square.

In all the cases, the total irradiated area may vary from 10 mm$^2$ to up to 250 mm$^2$, according to the number of holes and their diameter or cross dimensions.

Figure 9:
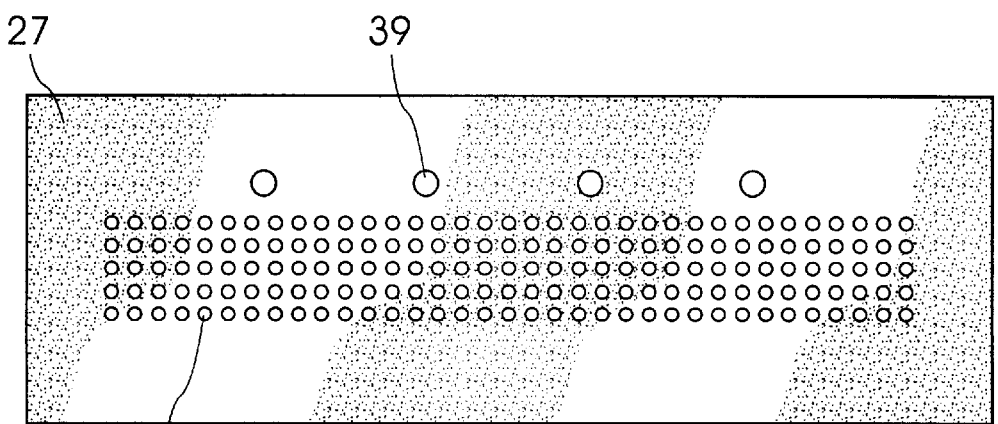

FIG. 9 of the drawings shows finally a modular mask element 27, suitable for treating large surface areas which can ideally be divided into portions of surfaces of equal dimensions. In this case the mask element 27 has an elongated rectangular shape, with a plurality of holes 38 aligned on several parallel rows. On one longitudinal side of the perforated zone the mask element 27 is provided with reference signs, for example in the form of holes 39 of greater dimensions, evenly spaced apart one from the other with a pitch corresponding to a modular unit of surfaces to be treated individually. In this case too the radiated area of the perforated surface of each modular surface unit may vary within the values indicated previously.

From what has been said and shown, it is therefore clear that an apparatus have been provided for the controlled generation of ultraviolet rays which can be used in the focused micro stimulation of biological cell structures, whereby a concentrated beam of ultraviolet rays is used, within a band of frequencies having a high percentage content of UVB rays, in combination with a suitable non-reflecting masking element arranged peripherally around the surface area of the biological cell structure to be treated, and in which the various working parameters of the apparatus for generation of the ultraviolet ray beam can be adjusted or modified appropriately by means of a programmable control unit which controls the entire apparatus and its operation.

The intent in any case is that what has been said and shown with reference to the accompanying drawings has been given purely by way of an example and illustration of the general principles of the invention.

I claim:

1. An apparatus for the controlled generation of UV ultraviolet rays for a focused micro stimulation of a biological cell structure, comprising:
    an ultraviolet generator for generation of a ultraviolet ray beam having ultraviolet electromagnetic rays in a frequency band between 200 and 400 nm;
    a focusing means for focusing the ultraviolet ray beam on a restricted surface area of the biological cell structure; and
    energy control means for controlling the quantity of energy radiated on the restricted surface area, said energy control means comprising a mask element in non-reflecting material for encircling the restricted surface area of the biological cell structure, masking surrounding zones,
    wherein said ultraviolet generator is designed to provide a percentage content of electromagnetic rays in the frequency band between 260 and 300 nm, comprised between 60% and 85% of the total electromagnetic energy generated.

2. An apparatus according to claim 1, wherein said ultraviolet generator is designed to continuously generate an ultraviolet ray beam.

3. An apparatus according to claim 1, wherein said ultraviolet generator is designed to generate a ray beam in pulsed mode.

4. An apparatus according to claim 1, comprising control means to adjust the amplitude and the power of the ray beam.

5. An apparatus according to claim 1, wherein the mask element has a single central hole.

6. An apparatus according to claim 5, wherein said central hole has an area greater than 3 $mm^2$.

7. An apparatus according to claim 6, wherein said hole has an area of between 3 and 500 $mm^2$.

8. An apparatus according to claim 1, wherein the mask element has a plurality of holes.

9. An apparatus according to claim 8, wherein the mask element comprises holes of a same diameter.

10. An apparatus according to claim 8, wherein the mask element comprises holes having different diameters.

11. An apparatus according to claim 8, wherein said holes are arranged along one or more concentirc circumferences.

12. An apparatus according to claim 8, wherein the total surface area of the holes is greater than 10 $mm^2$.

13. An apparatus according to claim 12, wherein the total surface area of the holes is between 10 and 250 $mm^2$.

14. An apparatus for the controlled generation of UV ultraviolet rays for a focused micro stimulation of a biological cell structure, comprising:

an ultraviolet generator for generation of a ultraviolet ray beam having ultraviolet electromagnetic rays in a frequency band between 200 and 400 nm;

a focusing means for focusing the ultraviolet ray beam on a restricted surface area of the biological cell structure; and energy control means for controlling the quantity of energy radiated on the restricted surface area, said energy control means comprising a mask element in non-reflecting material for encircling the restricted surface area of the biological cell structure, masking surrounding zones, wherein the mask element has a plurality of holes, and the holes are parallely arranged along rows.

15. An apparatus according to claim 14, comprising modular perforated areas and reference elements for said modular areas evenly spaced apart on one side of rows of holes.

16. An apparatus according to claim 14, wherein the total surface area of the holes is greater than 10 $mm^2$.

17. An apparatus according to claim 14, comprising a light filter device for the emission of a fluorescent light, which can be positioned in front of the ray beam focusing means.

18. An apparatus for the controlled generation of UV ultraviolet rays for a focused micro stimulation of a biological cell structure, comprising:

an ultraviolet generator for generation of a ultraviolet ray beam having ultraviolet electromagnetic rays in a frequency band between 200 and 400 nm;

a focusing means for focusing the ultraviolet ray beam on a restricted surface area of the biological cell structure;

energy control means for controlling the quantity of energy radiated on the restricted surface area, said energy control means comprising a mask element in non-reflecting material for encircling the restricted surface area of the biological cell structure, masking surrounding zones; and a light filter device for the emission of a fluorescent light, which can be positioned in front of the ray beam focusing means.

19. An apparatus according to claim 8, wherein said ultraviolet generator is designed to provide a percentage content of electromagnetic rays in the frequency band between 260 and 300 nm, comprised between 60% and 85% of the total electromagnetic energy generated.

20. An apparatus according to claim 18, wherein the mask element has a plurality of holes, wherein the total surface area of the holes is greater than 10 $mm^2$.

* * * * *

UNITED STATES PATENT AND TRADEMARK OFFICE
CERTIFICATE OF CORRECTION

PATENT NO. : 6,645,231 B1  Page 1 of 1
DATED : November 11, 2003
INVENTOR(S) : Franco Caldironi It is certified that error appears in the above-identified patent and that said Letters Patent is hereby corrected as shown below:

Column 8,
Line 32, change "claim 8" to -- claim 18 --.

Signed and Sealed this

Seventeenth Day of February, 2004

JON W. DUDAS
*Acting Director of the United States Patent and Trademark Office*